United States Patent
King

(10) Patent No.: US 11,067,576 B2
(45) Date of Patent: Jul. 20, 2021

(54) METHOD FOR HEALTH MAINTENANCE MONITORING

(71) Applicant: Martin King, Hackettstown, NJ (US)

(72) Inventor: Martin King, Hackettstown, NJ (US)

(*) Notice: Subject to any disclaimer, the term of this patent is extended or adjusted under 35 U.S.C. 154(b) by 0 days.

(21) Appl. No.: 15/916,341

(22) Filed: Mar. 9, 2018

(65) Prior Publication Data
US 2018/0259525 A1 Sep. 13, 2018

Related U.S. Application Data

(60) Provisional application No. 62/469,098, filed on Mar. 9, 2017.

(51) Int. Cl.
| | |
|---|---|
| *G01N 33/574* | (2006.01) |
| *C12Q 1/6886* | (2018.01) |
| *G01N 33/72* | (2006.01) |
| *G01N 33/50* | (2006.01) |
| *C12Q 1/6883* | (2018.01) |

(52) U.S. Cl.
CPC ......... *G01N 33/574* (2013.01); *C12Q 1/6883* (2013.01); *C12Q 1/6886* (2013.01); *G01N 33/5002* (2013.01); *G01N 33/5091* (2013.01); *G01N 33/721* (2013.01); *C12Q 2600/156* (2013.01); *C12Q 2600/158* (2013.01)

(58) Field of Classification Search
CPC ............. G01N 33/574; G01N 33/5091; G01N 33/5002; G01N 33/721; C12Q 1/6883; C12Q 1/6886; C12Q 2600/156; C12Q 2600/158

See application file for complete search history.

(56) References Cited

PUBLICATIONS

Rehak—Storage of Whole Blood Effect of Temperature on the Measured COncentration of Analytes in Serum—Clin Chem—1988 (Year: 1988).*
Mutter—Comparison of frozen and RNALater solid tissue storage methods for use in RNA expression microarrays—2004 (Year: 2004).*
Rehak—Phtolysis of bilirubin in serum specimens exposed to room lighting—2008 (Year: 2008).*
Dirar—Effect of Storage Time and Temperature on some serum analytes—International Journal of Pathology—2010 (Year: 2010).*
Vaught—Biological sample collection, processing, storage and information management—IARC—2011 (Year: 2011).*

(Continued)

*Primary Examiner* — Benjamin R Whatley
*Assistant Examiner* — Jean Caraballo-Leon
(74) *Attorney, Agent, or Firm* — Benjamin Appelbaum

(57) ABSTRACT

A method for monitoring health maintenance by collecting an initial blood sample from an individual and dividing the collected blood sample into at least two parts. The first of the two parts is immediately analyzed for multiple blood components levels, and the second part is frozen immediately after the collection to be used at a later time as a comparative standard. After a period of time, a second blood sample is collected from the same individual and analyzed for the same multiple blood components levels in a parallel test with the frozen part. The results obtained from the second blood sample are then compared to the results from the frozen comparative standard to detect real changes in the multiple blood components levels over time.

6 Claims, 19 Drawing Sheets

(56) References Cited

PUBLICATIONS

Yang—Effect of Blood Sampling Processing and Storage on the Measurement of CAB—American Journal of Clinical Pathology—2015 (Year: 2015).*
Bergmann—The influence of sample freeezing at −80 for 2-12 weeks on glycated hemoglobin concentration assayed by HPLC—2016 (Year: 2016).*
Huang—Effects of storage temperature duration of blood samples on DNA and RNA—Plos One—2017 (Year: 2017).*
Nunez—Frozen sections of samples taken intraoperatively for diagnosis of infection in revision hip surgery—Acta Orthopedica—2007 (Year: 2007).*
Huang et al (Aspartate Aminotransferase (AST/GOT) and Alanine Aminotransferase (ALT/GPT) Detection Techniques, Sensors, 6, 2006, pp. 756-782) (Year: 2006).*
WHO (Who Guidelines on Drawing Blood: Best Practies in Phlebotomy, World Health Organization, 2010) (Year: 2010).*
WHI (Section 11—Blood and Urine Collection, Processing and Shipment, Women's Health Initiative Manuals: Volume 2—Procedures, 1997, Document Accession: phd001961.1) (Year: 1997).*
Maharam (Running Doc says taking 72 hrs off before annual physical can help prevent false reports, NY Daily News Website, 2015, 6 pages) (Year: 2015).*
Purvula, E, What's with the precision? Downloaded from the Internet from https://validationmanager.com/category/validation-blog, May 7, 2017.
Little. R.R., Rohling, C and Sacks, D.B The NGSP: Over 20 Years of Improving HbA1c Measurement. 2019. Published in final edited form as Clin. Chem. Jul. 2019: 65(7):839-848, and published online Dec. 5, 2018, doi: 10.1373/clinchem.2018.296962.

* cited by examiner

FIG. 1(a)

| Sample Number | AM | PM | % Decrease |
|---|---|---|---|
| 1 | 0.76 | 0.754 | 1 |
| 2 | 3.06 | 2.065 | 33 |
| 3 | 2.69 | 2.07 | 23 |
| 4 | 1.94 | 0.99 | 49 |
| 5 | 0.57 | 0.431 | 24 |
| 6 | 1.60 | 1.12 | 30 |
| 7 | 4.12 | 2.78 | 33 |
| 8 | 2.65 | 1.70 | 36 |
| 9 | 1.63 | 1.37 | 16 |
| 10 | 2.85 | 2.05 | 28 |
| 11 | 1.76 | 1.63 | 7 |
| 12 | 1.38 | 0.85 | 38 |
| 13 | 1.85 | 1.57 | 15 |
| 14 | 1.58 | 1.407 | 11 |
| 15 | 2.01 | 1.38 | 31 |
| 16 | 1.23 | 1.21 | 2 |
| 17 | 1.01 | 0.95 | 6 |
| 18 | 2.31 | 1.65 | 29 |
| 19 | 2.24 | 1.47 | 34 |
| 20 | 0.97 | 0.88 | 9 |
| 21 | 1.73 | 1.12 | 35 |
| 22 | 6.54 | 5.13 | 22 |
| 23 | 0.63 | 0.48 | 24 |
| 24 | 3.90 | 2.89 | 26 |
| 25 | 1.38 | 1.08 | 22 |

FIG. 1 (b)

| Sample Number | AM | PM | % Decrease/Increase |
|---|---|---|---|
| 1 | 111.3 | 97.0 | -13 |
| 2 | 84.9 | 78.0 | -8 |
| 3 | 125.1 | 135.4 | +8 |
| 4 | 141.6 | 127.3 | -11 |
| 5 | 116.5 | 102.7 | -12 |
| 6 | 100.8 | 97.7 | -3 |
| 7 | 136.5 | 109.5 | -20 |
| 8 | 80.7 | 68.6 | -15 |
| 9 | 127.5 | 109.7 | -14 |
| 10 | 86.9 | 82.4 | -21 |
| 11 | 87.9 | 70.4 | -20 |
| 12 | 106.2 | 84.4 | -21 |
| 13 | 96.8 | 100.3 | +4 |
| 14 | 79.6 | 72.1 | -9 |
| 15 | 100.6 | 78.6 | -22 |
| 16 | 113.9 | 93.3 | -18 |
| 17 | 123.4 | 109.3 | -11 |
| 18 | 93.9 | 84.6 | -10 |
| 19 | 78.7 | 86.1 | +9 |
| 20 | 136.6 | 108.9 | -20 |
| 21 | 76.5 | 64.2 | -16 |
| 22 | 63.0 | 60.7 | -4 |
| 23 | 121.5 | 98.8 | -19 |
| 24 | 67.4 | 71.9 | +7 |
| 25 | 70.2 | 58.9 | -16 |

FIG. 1(c)

| Sample Number | AM | PM | % Decrease/Increase |
|---|---|---|---|
| 1 | 142 | 92 | -35 |
| 2 | 36 | 50 | +39 |
| 3 | 68 | 117 | +72 |
| 4 | 94 | 122 | +30 |
| 5 | 27 | 21 | -22 |
| 6 | 122 | 64 | -48 |
| 7 | 32 | 33 | +3 |
| 8 | 70 | 67 | -4 |
| 9 | 84 | 82 | -2 |
| 10 | 93 | 79 | -15 |
| 11 | 24 | 15 | -37 |
| 12 | 77 | 76 | -1 |
| 13 | 83 | 59 | -29 |
| 14 | 93 | 66 | -29 |
| 15 | 126 | 124 | -2 |
| 16 | 79 | 55 | -30 |
| 17 | 94 | 54 | -43 |
| 18 | 63 | 86 | +37 |
| 19 | 69 | 59 | -14 |
| 20 | 162 | 174 | +7 |
| 21 | 187 | 131 | -30 |
| 22 | 85 | 62 | -27 |
| 23 | 152 | 76 | -50 |
| 24 | 88 | 54 | -39 |
| 25 | 80 | 92 | +15 |

FIG. 1(d)

| Sample Number | AM | PM | % Decrease/Increase |
|---|---|---|---|
| 1 | 232 | 245 | +6 |
| 2 | 37 | 39 | +5 |
| 3 | 419 | 433 | +3 |
| 4 | 81 | 54 | -33 |
| 5 | 43 | 30 | -30 |
| 6 | 27 | 22 | -19 |
| 7 | 47 | 30 | -36 |
| 8 | 23 | 15 | -35 |
| 9 | 261 | 148 | -43 |
| 10 | 246 | 225 | -9 |
| 11 | 281 | 177 | -37 |
| 12 | 47 | 32 | -32 |
| 13 | 31 | 23 | -26 |
| 14 | 25 | 17 | -32 |
| 15 | 58 | 47 | -19 |
| 16 | 416 | 338 | -19 |
| 17 | 353 | 226 | -36 |
| 18 | 259 | 128 | -36 |
| 19 | 47 | 33 | -30 |
| 20 | 71 | 76 | +7 |
| 21 | 73.1 | 76.9 | +5 |
| 22 | 15.5 | 18.3 | +18 |
| 23 | 53.9 | 48.5 | -10 |
| 24 | 26.9 | 20.6 | -23 |
| 25 | 81.4 | 73.2 | -10 |

FIG. 1(e)

| Sample Number | AM | PM | % Decrease/Increase |
|---|---|---|---|
| 1 | 15.7 | 8.7 | -45 |
| 2 | 10.7 | 10.9 | +2 |
| 3 | 12.3 | 8.12 | -34 |
| 4 | 12.2 | 5.6 | -44 |
| 5 | 11.6 | 5.3 | -44 |
| 6 | 14.2 | 7.5 | -47 |
| 7 | 13.3 | 5.6 | -42 |
| 8 | 13.8 | 10.4 | -25 |
| 9 | 10.6 | 6.9 | -35 |
| 10 | 11.7 | 5.8 | -50 |
| 11 | 16.0 | 13.2 | -17 |
| 12 | 12.0 | 9.1 | -24 |
| 13 | 8.4 | 5.4 | -36 |
| 14 | 7.6 | 7.3 | -4 |
| 15 | 13.9 | 7.9 | -43 |
| 16 | 5.66 | 4.4 | -22 |
| 17 | 9.52 | 8.5 | -11 |
| 18 | 11.5 | 10.3 | -11 |
| 19 | 18.2 | 8.9 | -51 |
| 20 | 4.85 | 9.8 | +100 |
| 21 | 13.8 | 7.0 | -49 |
| 22 | 9.4 | 9.0 | -4 |
| 23 | 12.2 | 6.9 | -43 |
| 24 | 9.7 | 5.9 | -39 |
| 25 | 16.7 | 9.7 | -42 |

FIG. 2(a)

| Sample Number | Before Light Exposure | After Light Exposure (1 day) | % Decrease |
|---|---|---|---|
| 1 | 0.4 | 0.1 | 75 |
| 2 | 0.4 | 0.1 | 75 |
| 3 | 0.5 | 0.1 | 80 |
| 4 | 0.9 | 0.2 | 78 |
| 5 | 0.4 | 0.1 | 75 |

FIG. 2(b)

| Sample Number | Before Light Exposure | After Light Exposure (2 days) | % Decrease |
|---|---|---|---|
| 1 | 1.4 | 1.3 | 7 |
| 2 | 1.9 | 1.8 | 5 |
| 3 | 3.5 | 3.4 | 3 |
| 4 | 7.6 | 7.4 | 3 |
| 5 | 1.9 | 1.8 | 5 |
| 6 | 1.4 | 1.4 | 0 |
| 7 | 1.4 | 1.4 | 0 |
| 8 | 1.7 | 1.7 | 0 |
| 9 | 1.4 | 1.3 | 7 |
| 10 | 1.4 | 1.3 | 7 |

FIG. 3

|  | Potassium | | LDH | | Phosphorus | | Glucose | |
| --- | --- | --- | --- | --- | --- | --- | --- | --- |
|  | Sample 1 | Sample 2 | Sample 1 | Sample 2 | Sample 1 | Sample 2 | Sample 1 | Sample 2 |
| 0 hours | 4.7 | 4.1 | 116 | 154 | 2.4 | 2.6 | 167 | 73 |
| 8 hours | 4.7 | 4.0 | 122 | 165 | 2.2 | 2.5 | 150 | 59 |
| 24 hours | ---- | 4.4 | 129 | 196 | 1.9 | 3.7 | 104 | 35 |
| 48 hours | 5.5 | 6.1 | 183 | 243 | 4.3 | 10.9 | 63 | 2 |

FIG. 4

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 43 | 43 | 40 | 29 | 29 |
| 2 | 80 | 79 | 75 | 49 | 49 |
| 3 | 47 | 46 | 46 | 73 | 74 |
| 4 | 34 | 39 | 33 | | |
| 5 | 52 | 55 | 52 | | |
| 6 | 44 | 47 | 43 | | |
| 7 | 54 | 55 | 61 | | |
| 8 | 85 | 88 | 82 | | |
| 9 | 62 | 64 | 73 | | |
| 10 | 46 | 47 | 51 | | |
| 11 | 47 | 50 | 52 | | |
| 12 | 51 | 49 | 55 | | |
| 13 | 52 | 55 | 56 | | |
| 14 | 49 | 51 | 52 | | |
| 15 | 37 | 39 | 40 | | |
| 16 | 37 | 40 | 31 | | |
| 17 | 65 | 69 | 70 | | |
| 18 | 56 | 59 | 59 | | |
| 19 | 71 | 74 | 77 | | |
| 20 | 45 | 48 | 51 | | |

FIG. 5

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 3.7 | 3.6 | 4.1 | 3.3 | 3.3 |
| 2 | 4.5 | 4.4 | 4.4 | 5.7 | 5.7 |
| 3 | 6.5 | 6.3 | 7.2 | 9.5 | 9.4 |
| 4 | 7.2 | 7.0 | 7.9 | | |
| 5 | 6.6 | 6.4 | 6.6 | | |
| 6 | 3.8 | 3.8 | 4.4 | | |
| 7 | 5.9 | 5.8 | 5.7 | | |
| 8 | 4.8 | 4.8 | 4.8 | | |
| 9 | 5.2 | 5.1 | 4.8 | | |
| 10 | 6.7 | 6.6 | 7.5 | | |
| 11 | 6.4 | 6.4 | 6.5 | | |
| 12 | 6.5 | 5.9 | 7.6 | | |
| 13 | 3.8 | 3.8 | 4.5 | | |
| 14 | 4.3 | 4.3 | 4.5 | | |
| 15 | 6.1 | 6.1 | 5.8 | | |
| 16 | 5.2 | 5.1 | 4.6 | | |
| 17 | 5.0 | 5.0 | 4.8 | | |
| 18 | 4.3 | 4.3 | 4.6 | | |
| 19 | 4.0 | 4.0 | 4.6 | | |
| 20 | 6.1 | 6.1 | 5.9 | | |

FIG. 6

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 11 | 11 | 20 | 26 | 26 |
| 2 | 15 | 14 | 12 | 68 | 69 |
| 3 | 21 | 20 | 18 | 70 | 71 |
| 4 | 43 | 41 | 40 | | |
| 5 | 24 | 23 | 21 | | |
| 6 | 20 | 20 | 15 | | |
| 7 | 24 | 24 | 25 | | |
| 8 | 15 | 15 | 15 | | |
| 9 | 9 | 9 | 10 | | |
| 10 | 19 | 19 | 18 | | |
| 11 | 15 | 15 | 17 | | |
| 12 | 21 | 20 | 21 | | |
| 13 | 8 | 9 | 9 | | |
| 14 | 48 | 47 | 48 | | |
| 15 | 22 | 22 | 21 | | |
| 16 | 25 | 26 | 20 | | |
| 17 | 22 | 22 | 24 | | |
| 18 | 14 | 14 | 16 | | |
| 19 | 15 | 15 | 17 | | |
| 20 | 27 | 26 | 31 | | |

FIG. 7

| Sample Number | Initial Sample | Samples run in parallel | | Controls run in parallel | |
| --- | --- | --- | --- | --- | --- |
| | | Initial Sample (frozen) | Second Sample (3 months later) | First Control | Second Control |
| 1 | 20 | 21 | 30 | 36 | 36 |
| 2 | 12 | 16 | 15 | 92 | 92 |
| 3 | 15 | 18 | 13 | 202 | 203 |
| 4 | 14 | 16 | 16 | | |
| 5 | 33 | 34 | 34 | | |
| 6 | 24 | 24 | 24 | | |
| 7 | 37 | 37 | 23 | | |
| 8 | 19 | 19 | 19 | | |
| 9 | 17 | 18 | 21 | | |
| 10 | 16 | 16 | 16 | | |
| 11 | 18 | 18 | 17 | | |
| 12 | 27 | 25 | 33 | | |
| 13 | 11 | 11 | 13 | | |
| 14 | 58 | 59 | 73 | | |
| 15 | 11 | 11 | 13 | | |
| 16 | 20 | 20 | 13 | | |
| 17 | 20 | 20 | 25 | | |
| 18 | 24 | 25 | 22 | | |
| 19 | 17 | 17 | 42 | | |
| 20 | 21 | 21 | 20 | | |

FIG. 8

| Sample Number | Samples run in parallel | | | Controls run in parallel | |
|---|---|---|---|---|---|
| | Initial Sample | Initial Sample (frozen) | Second Sample (3 months later) | First Control | Second Control |
| 1 | 0.62 | 0.65 | 0.67 | 0.8 | 0.8 |
| 2 | 0.61 | 0.66 | 0.63 | 1.7 | 1.7 |
| 3 | 0.80 | 0.82 | 0.83 | 5.4 | 5.4 |
| 4 | 0.92 | 0.87 | 0.83 | | |
| 5 | 1.18 | 1.16 | 1.21 | | |
| 6 | 0.67 | 0.65 | 0.63 | | |
| 7 | 0.94 | 0.83 | 0.90 | | |
| 8 | 0.68 | 0.63 | 0.66 | | |
| 9 | 0.82 | 0.78 | 0.79 | | |
| 10 | 0.80 | 0.76 | 0.79 | | |
| 11 | 0.97 | 0.86 | 0.88 | | |
| 12 | 1.19 | 0.99 | 1.04 | | |
| 13 | 0.73 | 0.66 | 0.66 | | |
| 14 | 0.70 | 0.69 | 0.69 | | |
| 15 | 0.74 | 0.68 | 0.60 | | |
| 16 | 0.80 | 0.72 | 0.88 | | |
| 17 | 0.86 | 0.84 | 0.89 | | |
| 18 | 0.76 | 0.69 | 0.71 | | |
| 19 | 0.67 | 0.58 | 0.65 | | |
| 20 | 0.86 | 0.74 | 0.78 | | |

FIG. 9

| Sample Number | Initial Sample | Samples run in parallel | | Controls run in parallel | |
| --- | --- | --- | --- | --- | --- |
| | | Initial Sample (frozen) | Second Sample (3 months later) | First Control | Second Control |
| 1 | 21 | 21 | 18 | 15 | 15 |
| 2 | 16 | 15 | 9 | 40 | 40 |
| 3 | 13 | 13 | 11 | 69 | 69 |
| 4 | 14 | 14 | 15 | | |
| 5 | 25 | 24 | 21 | | |
| 6 | 19 | 19 | 11 | | |
| 7 | 25 | 25 | 23 | | |
| 8 | 13 | 13 | 13 | | |
| 9 | 16 | 16 | 20 | | |
| 10 | 13 | 12 | 14 | | |
| 11 | 18 | 18 | 15 | | |
| 12 | 24 | 21 | 21 | | |
| 13 | 10 | 10 | 11 | | |
| 14 | 13 | 12 | 13 | | |
| 15 | 10 | 9 | 10 | | |
| 16 | 12 | 12 | 9 | | |
| 17 | 14 | 14 | 12 | | |
| 18 | 11 | 11 | 15 | | |
| 19 | 22 | 21 | 16 | | |
| 20 | 14 | 13 | 13 | | |

FIG. 10

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 85 | 82 | 81 | 58 | 58 |
| 2 | 93 | 90 | 94 | 116 | 116 |
| 3 | 193 | 183 | 128 | 343 | 344 |
| 4 | 79 | 77 | 96 | | |
| 5 | 106 | 110 | 92 | | |
| 6 | 85 | 84 | 78 | | |
| 7 | 99 | 96 | 104 | | |
| 8 | 96 | 94 | 93 | | |
| 9 | 79 | 79 | 99 | | |
| 10 | 120 | 117 | 132 | | |
| 11 | 95 | 94 | 92 | | |
| 12 | 106 | 93 | 94 | | |
| 13 | 98 | 95 | 84 | | |
| 14 | 80 | 80 | 89 | | |
| 15 | 87 | 84 | 96 | | |
| 16 | 103 | 102 | 101 | | |
| 17 | 93 | 92 | 89 | | |
| 18 | 98 | 97 | 96 | | |
| 19 | 93 | 92 | 94 | | |
| 20 | 104 | 100 | 108 | | |

FIG. 11

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 103 | 104 | 107 | 78 | 78 |
| 2 | 104 | 104 | 105 | 100 | 100 |
| 3 | 105 | 105 | 105 | 122 | 122 |
| 4 | 102 | 102 | 101 | | |
| 5 | 100 | 102 | 104 | | |
| 6 | 105 | 107 | 107 | | |
| 7 | 103 | 104 | 104 | | |
| 8 | 103 | 106 | 104 | | |
| 9 | 103 | 105 | 105 | | |
| 10 | 105 | 104 | 105 | | |
| 11 | 100 | 101 | 103 | | |
| 12 | 102 | 95 | 104 | | |
| 13 | 106 | 106 | 104 | | |
| 14 | 103 | 103 | 102 | | |
| 15 | 103 | 102 | 103 | | |
| 16 | 104 | 102 | 106 | | |
| 17 | 103 | 102 | 106 | | |
| 18 | 101 | 100 | 101 | | |
| 19 | 105 | 104 | 103 | | |
| 20 | 110 | 108 | 107 | | |

FIG. 12

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 4.5 | 4.4 | 5.4 | 2.7 | 2.7 |
| 2 | 4.4 | 4.7 | 4.7 | 4.1 | 4.1 |
| 3 | 4.2 | 4.2 | 4.6 | 7.5 | 7.5 |
| 4 | 4.5 | 4.4 | 4.1 | | |
| 5 | 4.9 | 4.8 | 4.7 | | |
| 6 | 5.6 | 5.6 | 5.6 | | |
| 7 | 4.6 | 4.5 | 4.9 | | |
| 8 | 5.1 | 5.2 | 5.2 | | |
| 9 | 4.3 | 4.3 | 4.9 | | |
| 10 | 4.7 | 4.6 | 4.5 | | |
| 11 | 4.8 | 4.8 | 4.6 | | |
| 12 | 5.5 | 5.1 | 5.0 | | |
| 13 | 5.0 | 4.9 | 4.9 | | |
| 14 | 4.3 | 4.3 | 4.6 | | |
| 15 | 4.9 | 4.9 | 4.3 | | |
| 16 | 4.4 | 4.3 | 5.3 | | |
| 17 | 4.5 | 4.4 | 4.7 | | |
| 18 | 3.8 | 3.8 | 4.6 | | |
| 19 | 4.0 | 3.9 | 4.3 | | |
| 20 | 4.8 | 4.7 | 4.6 | | |

FIG. 13

| Sample Number | Initial Sample | Samples run in parallel | | Controls run in parallel | |
| --- | --- | --- | --- | --- | --- |
| | | Initial Sample (frozen) | Second Sample (3 months later) | First Control | Second Control |
| 1 | 3.0 | 3.3 | 2.0 | 5.0 | 5.0 |
| 2 | 0.8 | 0.8 | 0.8 | 26.2 | 26.2 |
| 3 | 1.4 | 1.6 | 6.1 | 45.8 | 45.8 |
| 4 | 2.6 | 2.7 | 3.9 | | |
| 5 | 2.2 | 2.2 | 1.4 | | |
| 6 | 4.7 | 4.6 | 2.6 | | |
| 7 | 0.6 | 0.6 | 0.6 | | |
| 8 | 0.9 | 0.9 | 0.7 | | |
| 9 | 4.1 | 4.0 | 1.8 | | |
| 10 | 1.0 | 1.0 | 2.4 | | |
| 11 | 2.9 | 2.8 | 2.1 | | |
| 12 | 37.6 | 33.2 | 3.9 | | |
| 13 | 0.7 | 0.6 | 1.6 | | |
| 14 | 1.9 | 1.8 | 1.3 | | |
| 15 | 5.3 | 5.2 | 3.9 | | |
| 16 | 8.7 | 8.5 | 7.8 | | |
| 17 | 3.5 | 3.4 | 4.4 | | |
| 18 | 0.7 | 0.6 | 0.8 | | |
| 19 | 1.8 | 1.7 | 1.8 | | |
| 20 | 7.5 | 7.3 | 5.5 | | |

FIG. 14

| Sample Number | Initial Sample | Samples run in parallel | | Controls run in parallel | |
|---|---|---|---|---|---|
| | | Initial Sample (frozen) | Second Sample (3 months later) | First Control | Second Control |
| 1 | 140 | 142 | 143 | 117 | 117 |
| 2 | 139 | 140 | 140 | 145 | 145 |
| 3 | 142 | 144 | 144 | 163 | 163 |
| 4 | 139 | 138 | 137 | | |
| 5 | 139 | 141 | 140 | | |
| 6 | 142 | 142 | 142 | | |
| 7 | 142 | 142 | 144 | | |
| 8 | 143 | 145 | 141 | | |
| 9 | 144 | 144 | 144 | | |
| 10 | 145 | 142 | 147 | | |
| 11 | 139 | 139 | 142 | | |
| 12 | 141 | 130 | 142 | | |
| 13 | 144 | 142 | 138 | | |
| 14 | 139 | 140 | 138 | | |
| 15 | 142 | 140 | 139 | | |
| 16 | 144 | 142 | 141 | | |
| 17 | 144 | 142 | 144 | | |
| 18 | 140 | 138 | 139 | | |
| 19 | 142 | 140 | 142 | | |
| 20 | 148 | 146 | 143 | | |

FIG. 15

| Blood Component | Mean | New method Precision Within Run 2 SD | Current Precision Between Run 2 SD | Times More Precise |
|---|---|---|---|---|
| Glucose | 115 | 2.6 | 6.1 | 2.3 |
| BUN | 40 | 1.0 | 2.6 | 2.6 |
| HDL | 49 | 1.4 | 4.0 | 2.9 |
| Uric Acid | 5.5 | 0.2 | 0.6 | 3.0 |
| Sodium | 145 | 1.1 | 4.0 | 3.6 |
| Chloride | 100 | 0.6 | 2.0 | 3.3 |
| AST | 36 | 1.2 | 2.2 | 1.8 |
| CRP | 5.1 | 0.1 | 0.6 | 6.0 |

METHOD FOR HEALTH MAINTENANCE MONITORING

BACKGROUND

This invention generally relates to the field of laboratory testing in humans.

Laboratory testing as a mechanism to diagnose diseases in humans has been used for more than a century. One of the first test methods published was by Dr. HenryBence-Jones in the *Lancet* in 1847. It was a test for Bence-Jones protein (free light chains) in urine. This test continues to be used to the present day in helping to diagnose multiple myeloma. Over the years, laboratory tests have increased in quantity and quality. Today, hundreds of tests are available that help diagnose and monitor numerous diseases. These tests are performed on patients in hospitals, clinics, commercial laboratories, physician offices, etc. When performed correctly, such tests give useful information to physicians treating patients and help in monitoring patients progress.

However, the results of laboratory tests are often affected by numerous factors resulting in the physician receiving false or misleading information. Factors affecting test results can be separated into two main categories, namely, Type I and Type II.

Type I includes variations caused by how the patient is prepared for the sample collection and how the sample is handled after it has been taken from the patient. A list of some such variable factors are given in items A-J, as follows:

A. Time of day that the blood sample is drawn (as illustrated in FIGS. 1(*a*)-1(*e*));

B. Whether or not a patient is fasting and for how long, blood glucose, and lipids are greatly affected by fasting;

C. Whether or not the patient as exercised within a few days/hours of the blood sample being drawn;

D. The patient's diet;

E. What medication the patient may be taking;

F. Whether or not the patient's sample has been exposed to daylight and for how long (as illustrated in FIGS. 2(*a*)-2(*b*));

G. How the patient's sample is handled, stored, and transported to the laboratory (as illustrated in FIG. 3);

H. The state of hydration of the patient;

I. The position of the patient the blood sample is being drawn (recumbent or sitting); and J. The types of preservatives used in the blood collection tubes.

With respect to Factor A, FIGS. 1(*a*)-1(*e*) illustrate that the results in TSH, Total T3, Iron, Testosterone and Cortisol, respectively, vary depending on whether the blood sample was drawn from the patient in the morning or in the afternoon. Specifically, with respect to FIG. 1(*a*): blood samples were taken from 25 healthy young adults (males and females); blood was drawn between 7 am-9 am and again between 2 pm-4 pm; all samples showed a decrease from AM to PM; and average decline in TSH from AM to PM was 23%. Similarly, with respect to FIG. 1(*b*): blood samples e taken from 25 healthy young adults (males and females) between 7 am-9 am and again between 2 pm-4 pm; 4 samples showed an increase (#s 3, 13, 19, 24) and 21 samples showed a decline in results; average decline in Total T3 from AM to PM was 14%. Further, with respect to FIG. 1(*c*): blood samples were taken from 25 healthy young adults (males and females) between 7 am-9 am and again between 2 pm-4 pm; and serum iron shows variable results, i.e., increase in 7 samples and decrease in 18 samples.

Similarly, with respect to FIG. 1(*d*): blood samples were taken from 25 healthy young adults (males and females) between 7 am-9 am and again between 2 pm-4 pm; and testosterone shows variable results, i.e., increase in 6 samples and decrease in 19 samples. Finally, with respect to FIG. 1(*e*): blood samples were again taken from 25 healthy young adults (males and females) between 7 am-9 am and again between 2 pm-4 pm; and cortisol level has increased in 2 samples and decreased in 23 samples.

FIGS. 2(*a*) and 2(*b*) illustrate the effect of sunlight and fluorescent light (e.g., the light found in a typical refrigerator) on serum total bilirubin. As shown in these tables, sunlight breaks down total bilirubin, but the fluorescent light has little or no effect on total bilirubin.

Finally, FIG. 3 illustrates the effect of time passing between sample collection and sample separation. Blood samples were collected from two individuals, and cells were separated from serum immediately upon clotting (0 hours); after standing for 8 hours (8 hours); after standing for 24 hours (24 hours); and after standing for 48 hours (48 hours). Depending on the duration of time, false increases are seen in LDH, phosphorus, and potassium, while the glucose level decreases.

Accordingly, all Type I factors have the ability to negatively affect the test results and should be controlled and accounted for in laboratory testing environment. There is a need to minimize the variability of blood test results when they are being used to diagnose disease and to monitor disease progress or regression. However, when blood tests are being used to monitor health maintenance, the need for accuracy is even greater. Small changes need to be detected so that the individual can be assured that their health is stable and that their lifestyle of diet and exercise is succeeding in maintaining their health status. A standardized protocol must be used to minimize the variations listed above. Such a protocol will include standardization of the sampling time, patient position during phlebotomy, period of fasting, diet, hydration status, medications, exercise amount, and careful sample collection and handling.

This Application, however, is mainly concerned with Type II factors, i.e., factors affecting blood test results by the process of analysis performed in the laboratory. Additional variations in test results can be caused by technical factors, such as calibration changes, temperature variations, instrument problems, and/or errors caused by technical personnel. Such errors include inadequate mixing of samples, insufficient temperature equilibration, and possible mislabeling of samples, among others. Thus, there is a need to minimize such Type II factors in the analysis phase of the blood components, especially when blood tests are being used to monitor health maintenance, cancer recurrence, and diabetes and/or to detect early signs of organ damage in human clinical drug trials.

The health benefits of consistent and adequate exercise in humans is well known and documented, as are the benefits of a nutritious diet. Such benefits include significant reductions in heart disease, cancer, strokes, obesity, etc. However, the difficulty most humans have in consistently following an exercise and dietary protocol is equally well known.

There is a great need to have a scientifically based monitoring system a would encourage us to more stringently adhere to our diet and exercise goals.

SUMMARY OF THE INVENTION

It is an object of the present invention to provide a method for monitoring health maintenance while minimizing errors and increasing precision in the phase of analysis performed on the blood components.

It is also an object of the present invention to provide a method for monitoring health maintenance, which allows an individual to more precisely detect small incremental changes in test results.

In its general aspect, the invention is a method for monitoring health maintenance by collecting a blood sample from an individual and dividing the collected blood sample into at least two parts. The first of the two parts is immediately analyzed for multiple blood components levels, and the second part is frozen immediately after the collection to be used at a later time as a comparative standard. After a period of time, a second blood sample is collected from the same individual and analyzed for the same multiple blood components levels in a parallel test with the frozen part. The results obtained from the second blood sample are then compared to the results from the frozen comparative standard to detect real changes in the multiple blood components levels over time.

In one of its specific aspects, the step of freezing is performed at a temperature ranging from −30° C. to −85° C.; and more preferably at −80° C.

In another specific aspect, the step of analyzing the second blood sample is performed by utilizing the frozen part in a simultaneous parallel run with the collected second sample in order to detect changes in blood components.

In a further more specific aspect, the step of collecting the blood sample further comprises the steps of drawing a blood sample from the individual; allowing the blood sample to clot at a room temperature, while being wrapped in a non-light permeable material; and then centrifuging the clotted blood sample in a darkened centrifuge to obtain a serum sample.

This new method for monitoring health maintenance in adult humans improves the accuracy and precision of blood component testing and thereby allows the early detection of changes (both healthy and unhealthy) in these components. The detection of these changes allows a clear evaluation of the state of one's health. Both improvements, such as a decrease in a diabetic indicator, e.g. glucose, and unhealthy changes, such as increasing cholesterol levels, will be detected. Monitoring small changes in blood components allows improved control in the maintenance of health and also the early detection of health problems. This method will be utilized in a new type of health maintenance laboratory that will encourage individuals to monitor their health at 3 month intervals. It is anticipated that this scientific monitoring will encourage individuals to engage in a healthy lifestyle of exercise and dietary modification throughout their adult life.

The above aspects, advantages and features are of representative embodiments only. It should be understood that they are not to be considered limitations on the invention as defined by the claims. Additional features and advantages of the invention will become apparent in the following description, from the drawings, and from the claims.

BRIEF DESCRIPTION OF THE DRAWINGS

The invention is illustrated by way of examples which are not a limitation, and the figures of the accompanying drawings in which references denote corresponding parts, and in which:

FIGS. 1(a)-1(e) illustrate the results in TSH, Total T3, Iron, Testosterone and Cortisol, respectively, where the blood samples were drawn from the individuals in the morning and in the afternoon;

FIGS. 2(a) 2(b) illustrate the effect of sunlight and fluorescent light, respectively, on serum total bilirubin;

FIG. 3 illustrates the effect of time passing between sample collection and sample separation on LDH, phosphorus, potassium, and blood glucose;

FIGS. 4-14 illustrate that each analyte, i.e., HDL, Uric Acid, GGT, AST, Creatinine, BUN, Glucose, Chloride, Potassium, CRP, and Sodium, respectively, is unaffected by freezing at −80° C. for at least 3 months; and FIG. 15 illustrates that the new method changes the precision of the conducted tests from the between run precision to the within run precision.

DETAILED DESCRIPTION OF THE INVENTION

In accordance with the present invention, a new method of monitoring health maintenance is proposed that will allow individuals to more precisely see small incremental changes to their health. The method improves the precision level of the conducted blood tests from between run to within run precision, resulting in an improvement of twofold or more. The disclosed method will not only provide more accurate and precise blood testing, but will allow for personalized education and interpretation of results, and personalized advice on drug regimen, nutrition and exercise programs.

This patent application relates primarily to the blood testing component of the health monitoring system. Blood tests are performed in hospitals, clinics, physician offices, and large centralized commercial laboratories. For the most part, this type of testing when carefully performed is adequate for diagnosing and monitoring various disease states. This is due to the fact that the changes in the levels of blood components are generally large in disease states when compared to normal reference ranges.

However, when monitoring the status of healthy individuals or changes at the early stages of decease, a higher level of accuracy and precision is needed due to the fact that detection of smaller changes is required. This higher level of accuracy and precision is achieved with the described method.

In accordance with the preferred embodiment of the inventive method, a blood sample is first drawn from an individual. The sample is allow to clot (15 minutes) at room temperature, but is wrapped in non-light permeable material, e.g., aluminum foil, to protect some light sensitive components (e.g. bilirubin and vitamin A). The sample is then centrifuged preferably at 3,000 rpm in a darkened centrifuge for 15 minutes. After this, the serum is rapidly divided into 2 parts and placed in amber storage tubes. One part is placed into a deep freezer at approximately −80° C. The other part is analyzed within 4 hours for blood components such as: routine chemistry tests; Hemoglobin A1C; Vitamins; Homocysteine; C reactive protein; TSH; T4 free; Testosterone (total); DNA; RNA; etc. The part frozen at −80° C. is thawed out later, for example, 3 months later, and used as a comparative standard in the second analysis of the individual's blood. This method helps ensure that any changes in the blood components are real and not due to random or systemic errors in the analytical process. The use of the presently disclosed method results in improving the precision level of the conducted blood tests from between run to within run precision.

In an alternative embodiment, the entire blood sample, and not just the serum, is collected and divided into two parts, the second part of which is then frozen at −80° C. In this embodiment, blood components of the entire blood sample (including red cells and plasma) are analyzed in conducted tests.

In order to scientifically prove that each analyte is uneffected by freezing at −80° C. for 3 months, Applicant tested stability of 11 different analytes, i.e., HDL, Uric Acid, GGT, AST, Creatinine, BUN, Glucose, Chloride, Potassium, CRP, and Sodium. The results are shown in FIGS. 4-15. The data in the FIGS. 4-14 shows that all the listed analytes are stable at −80° C., See, Columns 2 and 3 in each Table. FIGS. 4-14 also show test results for the same blood components tested 3 months after the initial testing date, thus illustrating the inventive method.

More specifically, FIGS. 4-14 include data showing results of 11 blood component levels in 20 individuals: comparison of several types of samples, i.e., the initial sample, initial sample frozen for 3 months, fresh sample taken after a 3 month period, control sera run in parallel. The columns (numbered 1 through 6) indicate the following:

Column 1: sample number
Column 2: results for each component found on the initial test
Column 3: results for the same sample that was frozen at −80° C. for 3 months and then analyzed again in parallel with the second sample (taken 3 months later)
Column 4: results for second sample from the same individual taken 3 months later and analyzed in parallel with the initial frozen sample
Column 5: results from human control serum 1st sample
Column 6: results from human control serum 2nd sample The controls consist of human sera that have stable and fixed amounts of each analyte. When run in parallel these controls demonstrate the removal of almost all of the analytical variations that occur when samples are tested in separate runs. See the analytical variation that occurs between results in Column 2 (initial sample) and Column 3, same sample frozen and run 3 months later in a separate analytical run.

Since the initial frozen sample is analyzed in parallel with the second sample (taken 3 months later) under the same conditions, the Type II variations are minimized. Therefore, the second sample (column 4) result represents the real changes that have taken place in the individual's blood during the previous 3 months. These changes can he good or bad, e.g. had if the HDL level decreases since the higher the HDL level in blood, the lower the risk of a cardiac problem. The change can be good, e.g. if the glucose level decreases, since a decrease in glucose level indicates an improvement in the control of diabetes.

The new method changes the precision of the conducted tests from the between run precision to the within run precision. This result is more particularly illustrated in FIG. 15, which shows that, according to the conducted studies, the improvements in precision range from two-fold to six-fold depending on the test.

The inventive method is designed to be integrated into a sample collection protocol that will allow a significant improvement in the accuracy and precision of laboratory testing to be used in monitoring an individual's health status. The protocol consists of 10 steps that together with the invention will grant the ability to clearly measure changes in an individual's health status. The steps are as follows:

Sampling Protocol: In order to decrease variability in test results, a unique standardized protocol for obtaining and handling the blood sample is used. This protocol includes the following parameters:

1. One part of sample will be frozen at −80° C. immediately after the sample is obtained (within 15 minutes of blood draw) and this frozen sample will be utilized in the next sequence as a comparative standard that will he assayed in parallel with the then current sample.
2. Individual will fast for 12 hours.
3. Individual will maintain good hydration.
4. Individual will not exercise for 3 days prior to blood drawing.
5. A standard time will be used for blood drawing (in order to avoid diurnal variation).
6. Blood will be drawn using a collection system designed to minimize exposure to light (in order to protect against decay of vitamins and other light sensitive components)
7. No preservatives will be used in blood collection devices (as some of these may interfere with certain tests).
8. No transportation of blood samples will occur.
9. Tests will be performed within 4 hours of sample collection.
10. Phlebotomy chair will be used so that blood drawing occurs from a sitting position (not recumbent).

A new type of laboratory will preferably utilize the invention as described above. This laboratory will be local (thus avoiding transport of samples) and will incorporate blood monitoring, exercise programs and nutritional advice. The goal is to provide education, individual attention, and careful monitoring that will encourage participants to stay with the program for the long term (hopefully for life). The long term result should be improved health, decrease in serious illness, and a significant lessening of the costs of health care.

The new method is described above in connection with the process of health monitoring. However, the inventive method can also be utilized in monitoring organ function in clinical drug trials in order to detect early signs of organ damage. Further, the new method can also be used to monitor diabetics through Hemoglobin A1C assays. Finally, because of the high precision of the new method, it can also be used for early detection of cancer recurrence in patients who have had surgery, e.g. thyroid or prostate removal.

In the preceding specification, the invention has been described with reference to specific exemplary embodiments thereof. It will however, be evident that various modifications and changes may be made thereto without departing from the broader spirit and scope of the invention as set forth in the claims that follow. For example, the temperature at which the second half of the initial sample is frozen is indicated as −80° C. It should be understood by a person skilled in the art that this is a preferred temperature but a range of other freezing temperatures, for example from −30° C. to −85° C., can also be acceptable. The specification and drawings are accordingly to be regarded in an illustrative manner rather than a restrictive sense.

I claim as follows:

1. A method for monitoring health maintenance comprising the steps of:
    collecting an initial blood sample from an individual;
    dividing the collected blood sample into at least two parts;
    analyzing one part of said at least two parts of the collected sample for multiple blood components levels immediately after the collection, after allowing said one part of said divided collected blood sample to clot at a room temperature, while being wrapped in a non-light permeable material; and then centrifuging said clotted blood sample in a darkened centrifuge to obtain a serum sample and wherein said serum sample is tested for said multiple blood components levels;

freezing another part of said at least two parts of the collected sample at −80 C immediately after the collection and storing said frozen part to be used at a later time as a comparative standard;

collecting a second blood sample from said individual after a predetermined period of time;

analyzing said second blood sample for the same multiple blood components levels in a simultaneous parallel test with said frozen part and comparing said multiple blood components levels of said second blood sample to blood components levels of the stored comparative standard to detect changes in said multiple blood components levels over said predetermined period of time.

2. The method for monitoring health maintenance according to claim 1, wherein said multiple blood components comprise hemoglobin AIC, and wherein the step of collecting the second blood sample further comprises the steps of dividing the second blood sample into at least two portions, allowing one portion of the second blood sample to clot at a room temperature, while being wrapped in a non-light permeable material; then centrifuging the clotted portion of the second blood sample in a darkened centrifuge to obtain a serum sample and wherein said second blood sample serum sample is tested for said multiple blood components levels.

3. The method for monitoring health maintenance according to claim 1, wherein said multiple blood components comprise DNA, and wherein the step of comparing said multiple blood components levels comprises detecting mutated DNA over said predetermined period of time.

4. The method for monitoring health maintenance according to claim 1, wherein said multiple blood components comprise cancer markers, and wherein the step of comparing said multiple blood components levels comprises detecting cancer recurrence in patients.

5. A method for monitoring health maintenance, the method comprising the steps of:

collecting an initial blood sample from an individual;

allowing the collected blood sample to clot at a room temperature, while being wrapped in a non-light permeable material; and then centrifuging said clotted blood sample in a darkened centrifuge to obtain a serum sample;

dividing the collected serum sample into at least two parts;

analyzing one part of said at least two parts of the collected sample for one or more blood components levels immediately after the collection;

freezing another part of said at least two parts of the collected sample at −80° C. immediately after the collection and storing said frozen part for use as a comparative standard in a future test;

collecting a second blood sample from the individual after a specified period of time;

allowing the collected second blood sample to clot at a room temperature, while being wrapped in a non-light permeable material; and then centrifuging said clotted second blood sample in a darkened centrifuge to obtain a second serum sample;

analyzing said second serum sample for the same one or more blood components levels in a parallel test with said frozen part and comparing said one or more blood components levels of said second blood sample to the one or more blood components levels of the stored comparative standard to detect changes in said multiple blood components levels over said specified period of time;

the method resulting in an increase in precision in the range of 2-6 fold, precision being determined by analysis of data from a plurality of the blood tests of said multiple blood components.

6. A method to improve the precision of clinical laboratory testing, the method comprising the steps of:

collecting an initial blood sample from an individual;

dividing the collected blood sample into at least two parts;

analyzing one part of said at least two parts of the collected sample for one or more blood components levels immediately after the collection;

freezing another part of said at least two parts of the collected sample at immediately after the collection and storing said frozen part for use as a comparative standard in a future test;

collecting a second blood sample from the individual after a specified period of time;

analyzing said second blood sample for the same one or more blood components levels in a parallel test with said frozen part and comparing said one or more blood components levels of said second blood sample to the one or more blood components levels of the stored comparative standard to detect real changes in said multiple blood components levels over said specified period of time; and wherein the blood is drawn at a specific time of the day, using a blood collection system whose devices do not contain a preservative, and in said blood collection system exposure of the drawn blood to light is minimized, and wherein; and wherein the blood is drawn from an individual in a sitting position in a phlebotomy chair, and the individual has not exercised for 3 days prior to the time of the blood draw, and has fasted prior to the time of the blood draw;

wherein after the blood samples have been drawn, blood tests will be performed onsite, within 4 hours after sample collection, and wherein a portion of the sample is frozen at −80° C. within about 15 minutes after the blood is drawn, wherein the method results in an increase in precision of said multiple blood components in the range of about 2 to about 6 fold, precision being determined by analysis of data from a plurality of the blood tests of said multiple blood components.

* * * * *